(12) United States Patent
Ashby

(10) Patent No.: US 11,602,480 B2
(45) Date of Patent: Mar. 14, 2023

(54) VISUAL FIELD OBSERVATION TRAINING LENS

(71) Applicant: Brandon Ashby, Springville, UT (US)

(72) Inventor: Brandon Ashby, Springville, UT (US)

( * ) Notice: Subject to any disclaimer, the term of this patent is extended or adjusted under 35 U.S.C. 154(b) by 228 days.

(21) Appl. No.: 16/759,295

(22) PCT Filed: Aug. 10, 2018

(86) PCT No.: PCT/US2018/046341
§ 371 (c)(1),
(2) Date: Apr. 24, 2020

(87) PCT Pub. No.: WO2019/083591
PCT Pub. Date: May 2, 2019

(65) Prior Publication Data
US 2021/0177688 A1    Jun. 17, 2021

Related U.S. Application Data

(60) Provisional application No. 62/576,642, filed on Oct. 24, 2017.

(51) Int. Cl.
*A61H 5/00* (2006.01)
*A61F 9/02* (2006.01)
*G02C 7/10* (2006.01)

(52) U.S. Cl.
CPC ............... *A61H 5/00* (2013.01); *A61F 9/029* (2013.01); *G02C 7/10* (2013.01); *G02C 7/104* (2013.01); *G02C 7/105* (2013.01)

(58) Field of Classification Search
CPC .......... G02C 7/10; G02C 7/104; G02C 7/105; G02C 5/003; A61H 5/00; A61F 9/029
USPC .......... 351/41, 159.01, 159.02, 159.05, 159.1
See application file for complete search history.

(56) References Cited

U.S. PATENT DOCUMENTS

| | | |
|---|---|---|
| 5,428,409 A | 6/1995 | Silverstein |
| 5,592,698 A | 1/1997 | Woods |
| 2007/0046888 A1 | 3/2007 | Kurzrok |
| 2007/0285613 A1 | 12/2007 | Hobbs |

*Primary Examiner* — Tuyen Tra
(74) *Attorney, Agent, or Firm* — David B. Tingey; Bryant J. Keller; Kirton McConkie

(57) ABSTRACT

A visual field observation training lens is disclosed, along with corresponding training eyewear. An associated method for training visual observation toward a designated field of view is provided.

20 Claims, 14 Drawing Sheets

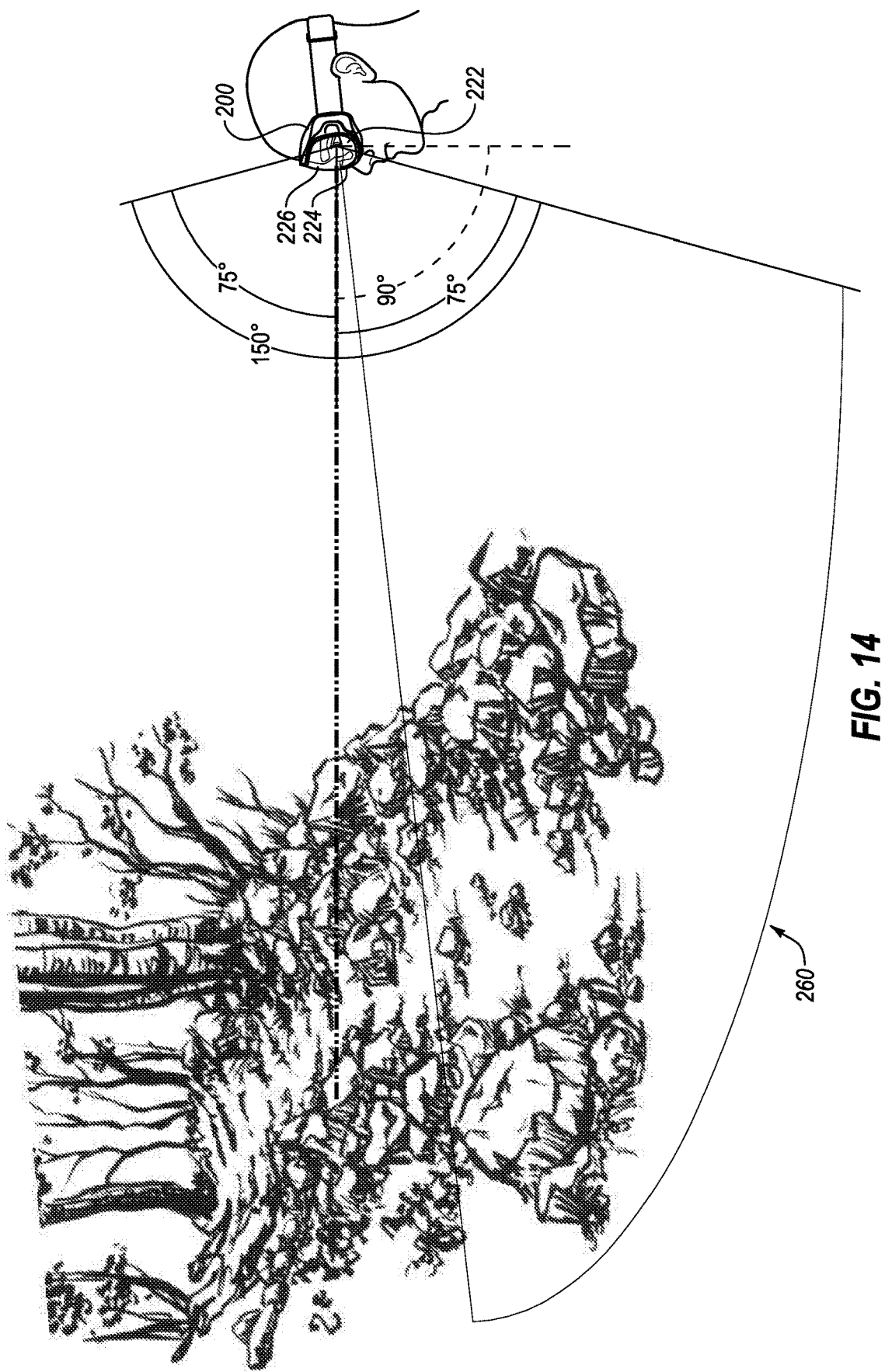

VISUAL FIELD OBSERVATION TRAINING LENS

CROSS REFERENCE TO RELATED APPLICATION

This application claims the benefit of U.S. Provisional Patent Application No. 62/576,642, filed Oct. 24, 2017, the disclosures of which are hereby incorporated entirely herein by reference.

BACKGROUND OF THE INVENTION

The Field of the Invention

The invention relates generally to active human perception of a visual field and more specifically to wearable lenses configured to help train visual observation toward a designated field of view.

The Relevant Technology

The way we perceive our surroundings can have significant impact on how effectively we perform various activities. Often, it can be advantageous to visually focus on certain narrowed aspects within a visual field, because observations particularly associated with the narrowed field of view can facilitate enhanced performance. For example, as we learn and increase our skills pertaining to activities such as playing a piano or typing, our performance often increases when we visually focus our observation more on the sheet music or screen, rather than looking at the keyboard. Visually focusing on printed music enhances performance related to playing many different musical instruments. In addition, many outdoor activities can be performed more effectively when visual focus is narrowed to an optimal field of view. For instance, activities such as motorcycle riding, motocross riding, mountain bike riding, snow skiing, snowboarding, timber sled (snow motorcycle) riding, snowmobile riding, hiking, ATV riding, UTV driving, rock climbing, downhill ice skating (ice cross), tightrope walking, slack-lining, skateboarding, off-road racing, etc., all include aspects associated with navigating a course or terrain. How such navigation is perceived, especially within a focused field of view, can significantly affect how quickly and efficiently the course or terrain may be traversed. Moreover, it can be advantageous to visually focus on a narrowed field of view and limit visual perception focus when engaging in physical rehabilitation, visual rehabilitation, speech rehabilitation, recuperating from a concussion, or participating in other motor-skill recovery activities, or teaching muscle memory generally. Furthermore, it can be beneficial to limit observable field of view for those struggling with vertigo or for aiding those with autism during movement activities and focused communication events. As such, there is a need for devices and methodology to focus and train active observation toward a designated field of view.

BRIEF SUMMARY OF THE INVENTION

It is a main object of the present invention to provide visual field observation training lens and corresponding methodology for observing a visual field.

A first disclosed aspect provides a visual field observation training lens comprising: a total surface area; a first transparency region; a second transparency region; wherein the second transparency region is less transparent than the first transparency region; and wherein the second transparency region comprises 10% to 70% of the total surface area of the training lens.

Another disclosed aspect provides eyewear for training user observation of a visual field, the eyewear comprising: a lens having bifurcated tinting; wherein a lower portion of the lens is more darkly tinted than an upper portion of the lens; and wherein the tinting bifurcation of the lens comprises a clear demarcation boundary, such that there is a significantly noticeable difference in observability between the lower more darkly tinted portion and the upper portion and a clear delineation between corresponding lens transparency associated with the lower darker tinted portion and the upper portion of the lens.

Moreover, a further disclosed aspect provides a method for training observation of a visual field, the method comprising: providing a lens having bifurcated tinting, the lens including: a total surface area; a first transparency region; and a second transparency region; wherein the first transparency region of the lens is more darkly tinted than the second transparency region of the lens; and wherein the tinting bifurcation of the lens comprises a clear demarcation, such that there is a significantly noticeable difference in observability between the first transparency region and the second more darkly tinted transparency region and a clear delineation between corresponding lens transparency associated with the first transparency region and the second more darkly tinted transparency region of the lens; incorporating the lens into eyewear; and wearing the eyewear and observing a visual field through the lens, such that a range of the field of view is significantly darkened by the tinted region of the lens to direct user perception toward a designated field of view.

These and other objects, aspects and features of the present invention will become more fully apparent from the following description and appended claims or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 14 illustrates a side view of a human profile wearing the embodiment of goggles having an embodiment of a training lens, and revealing a darkened range of view of the visual field of FIG. 13 including a darkened portion of the course or terrain that the human intends to traverse.

DETAILED DESCRIPTION OF THE PREFERRED EMBODIMENTS

Various aspects of the novel systems, apparatuses, and methods are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of, or combined with, any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different dispensers, some of which are illustrated by way of example in the figures and in the following description of the preferred aspects. The detailed description and drawings are merely illustrative of the disclosure rather than limiting, the scope of the disclosure being defined by the appended claims and equivalents thereof.

The attached drawings illustrate examples. Elements indicated by reference numbers in the attached drawings correspond to elements indicated by like reference numbers in the following description.

Figure 1:
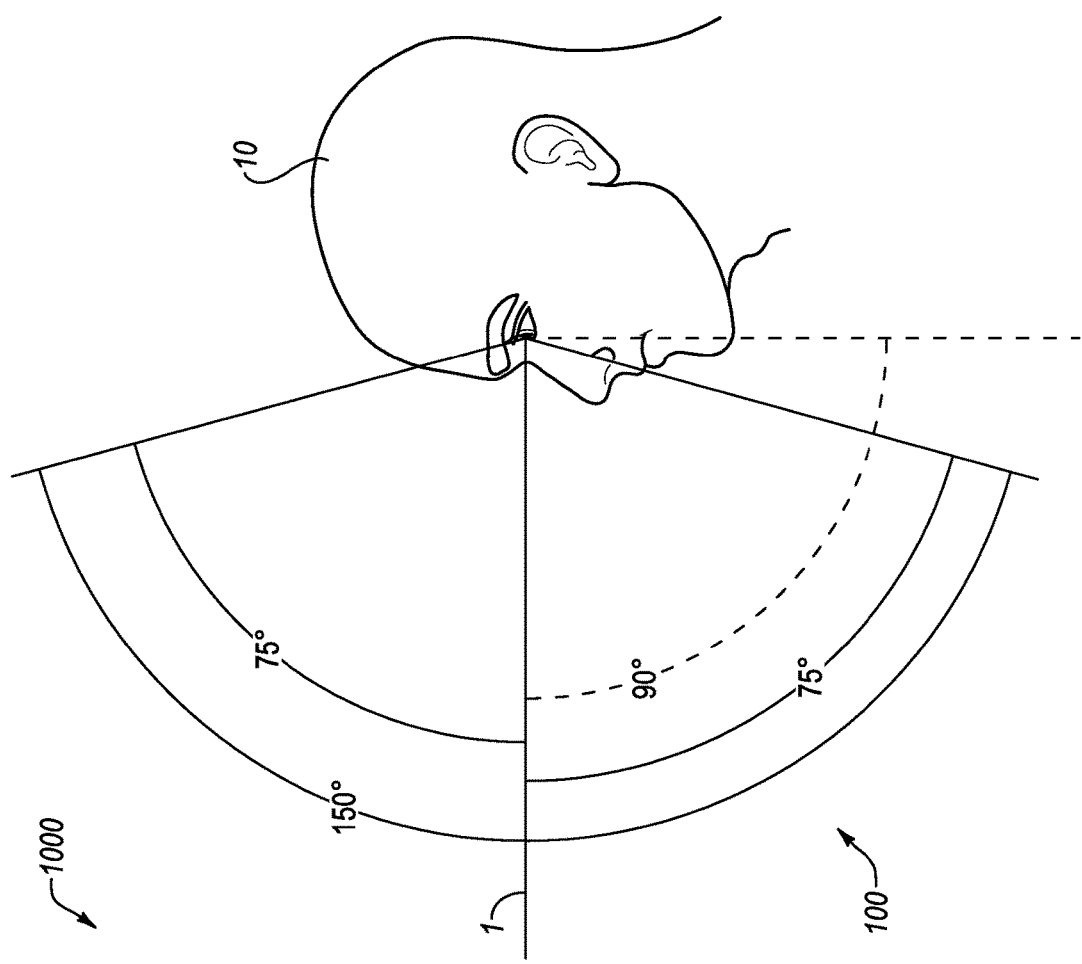
FIG. 1 illustrates a side view of a human profile revealing typical range of view of a visual field.

Referring to FIG. 1, a side view of a human profile 10 is depicted revealing typical range of view 100 of a visual field 1000. It is appreciated by those having ordinary skill in the relevant art, that the common, or average, vertical range 100 pertinent to a visual field 1000 observable by most humans is around 150 degrees. Of the common 150 degree vertical range 100, about half, or 75 degrees, of the field lies above a horizontal line of site axis 1 corresponding to the visual field 1000. The other half, or 75 degrees, extends downward from the horizontal line of site axis of the field. If a human directs a line of site at an angle other than horizontal (such as if a person is looking up or looking down), then the common 150 degree range 100 correspondingly rotates to adjust to the angle of the directed line of site, such that the line of site bifurcates the field of view 1000, with about 75 degrees observable both above and below the line of site. Thus, the common 150 degree vertical range 100 persists even when the line of site extends at an angle other than horizontal (or 90 degrees) in reference to the vertical frame of the human. As such, when a human looks at downward, with a line of site at an angle smaller than horizontal (or 90 degrees), it is possible that some portion of the field of view 1000 is encompassed by the visage of the human's own body.

When humans are engaged in various activities, it can be beneficial to keep a forward focus mindset on the activity in which they are engaged. For example, in many off-road sports, such as motorcycle riding, one of the key concepts that riders may learn is to keep their eyes (or the prominent focus of their line of site) focused on what is ahead, rather than what they are engaged in. This forward focus mindset allows the conscious mind to acknowledge what is ahead and then, by looking past, or extending the line of site beyond, an upcoming turn or obstacle, the subconscious mind of the rider is able to react and overcome without the conscious mind taking over and putting too much focus on the turn or obstacle. It has been proven in such riding activities that putting too much focus on an obstacle can actually tend to slow an individual down and even cause the individual to have more difficulty overcoming the obstacle than had the individual kept focused with a line of site on what was ahead. Forward focus may allow an individual to prepare for the next obstacle rather than focusing only on the current obstacle and then failing to efficiently traverse the next obstacle, because the individual did not effectively perceive the approach of the next obstacle.

Reading a trail, track or path may be the most important aspect of traversing a course, whether the traversal is accomplished on a bike, a motorized vehicle, skis, a snowboard, a skateboard, another traveling mechanism, or even on foot. There's a saying in racing, "The top racers are looking at a totally different track than everybody else." Of course, it's the same track, but the best racers are just seeing it differently than the others. The best racers are seeing solutions, while other racers are more focused on avoiding obstacles or navigating turns. For example, when training for race car driving, and individual may lose control and head toward a side wall, and with their focus completely on the wall, the individual may perceive ahead of time that they will hit it. During training, to overcome this loss of control, a good trainer may physically grab the head of the trainee and turn it to where the vehicle needs to go; the trainee, then forward focusing on the goal of traversing the course, rather than their fear of the wall, often resumes control, by pulling away from their previous path toward the approaching wall and back onto the course. Focusing forward, rather than letting visual perception dwell on approaching obstacles, helps aid a racer in overcoming course challenges naturally and easily.

Figure 2A:
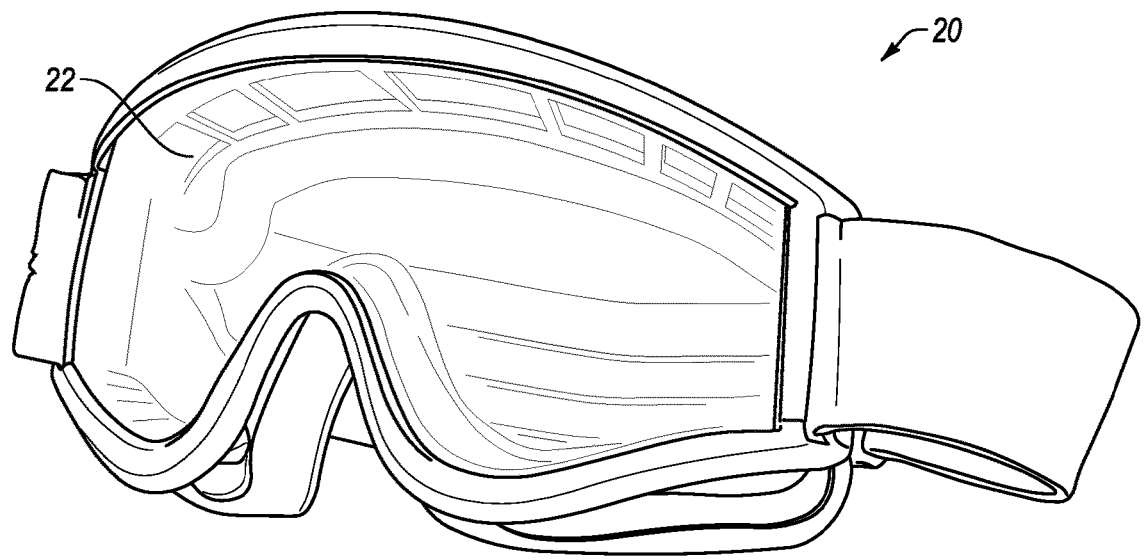
FIG. 2A illustrates a front perspective view of common riding goggles of the prior art.

Often racers, or individuals engaging in outdoor movement activities, wear eye protection, such as googles, helmet shields, or glasses. The eye protection may include tinting to help wearers focus more clearly on a visual field 1000, in sunlight, when there are glaring reflections, or when the ambient light associated with the visual field 1000 is bright and a tinting effect may aid or otherwise make observing the visual field 1000 easier and more effective. With continued reference to the drawings, FIG. 2A depicts a front perspective view of typical riding goggles 20, such as those common in the prior art. The goggles 20 include a lens 22. In the depicted embodiment, the lens 22 is not tinted. However, those of ordinary skill in the art will appreciate that the full lens 22 may be tinted.

Figure 2B:
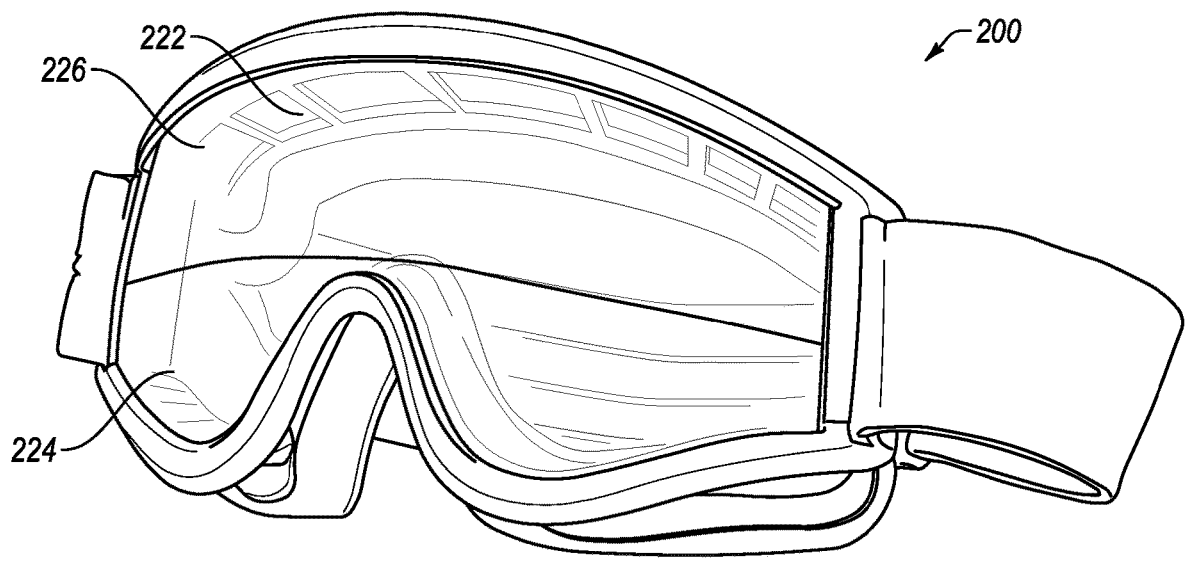
FIG. 2B illustrates a front perspective view of an embodiment of riding goggles including an embodiment of a training lens.

In stark contrast to the typical goggles 20, FIG. 2B depicts an embodiment of training goggles 200 including an embodiment of a training lens 222 having a total surface area and a tinted lower portion or region 224 and a non-tinted (or less-tinted) upper portion or region 226. The tinted lower portion or region 224 is less transparent than the upper portion or region 226. The tinted lower portion or region 224 may comprise more than 10% and less than 70% of the total surface area of the training lens 222. Additionally, the tinted lower portion or region may be situated on the training lens 222 such that roughly 10% to 85% of the of the field of view presented through the lens 222 to a wearer of the training goggles 200 is observable through the lower portion or region 224. Moreover, the degree of tinting of the tinted lower portion or region 224 on the training lens 222 may vary from light tinting (almost completely transparent) to dark tinting (affording much less transparency). The first more transparent upper portion or region 226 and second less transparent and more darkly tinted portion or region 224 have a visual light transmission value, wherein the difference between the visual light transmission of the first more transparent upper portion or region 226 and second less transparent and more darkly tinted portion or region 224 is between 20% and 80%. In addition, the tinting of the tinted lower portion or region 224 may comprise various colors and various types of tint. Furthermore, if no transparency is needed for effectively perceiving a visual field 1000 by a wearer of the goggles 200 during performance of an activity, the tinting may render complete non-transparency of the lower tinted portion or region 224, completely blocking out visual observation through the tinted lower portion or region 224 of the training lens 222 of the training goggles 200. The tinting of a lens may be formed by a film, a dye, a deposition layer, a darkened portion of a composite lens layer, a laser coating, chrome coating, electro plating, a snap/clip on layer, a sliding adjustable tinted layer, a color change in the lens between upper and lower portions of the lens, and/or any other like tinting process or combination of processes. The words "tint," "tinted," or "tinting, as used herein, may refer to a darker shade of VLT (visual light transmission) or to a different coloring of the lens with the same VLT between upper and lower portions of the lens 222, because there may be embodiments with equal transparency (VLT) that include a color change between the upper and lower portions or regions that facilitate the affect desired. A lens may be formed of a flexible material or a rigid material. The lens 222 may also be removable from the eyewear, such as the goggles 200, to which it is attached or into which it is incorporated. The lens 222 may be shatter-resistant. The lens 222 should be sufficiently transparent to allow a wearer of the lens to clearly perceive all aspects of an observed environment comprising a visual field. Where a lens is comprised of composite layers, the lower tinted portion or region 224 may be formed on one layer and the upper non-tinted (or much less tinted) portion or region 226 may be formed on another layer.

Figure 3:
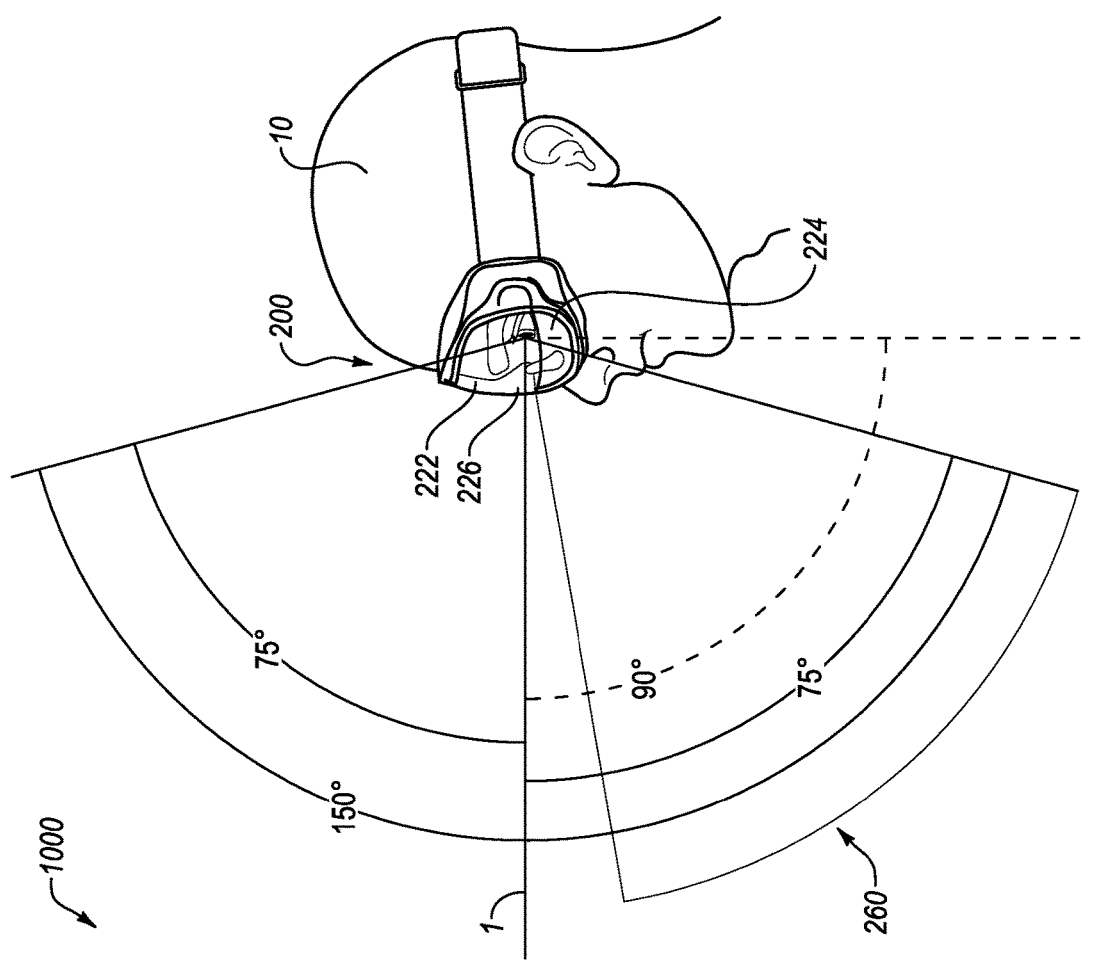
FIG. 3 illustrates a side view of a human profile wearing the embodiment of riding goggles of FIG. 2B having an embodiment of a training lens, and revealing a darkened range of view of a visual field.

Referring still further to the drawings, FIG. 3 depicts a side view of a human profile 10 wearing the embodiment of riding goggles 200 of FIG. 2B having an embodiment of a training lens 222, and revealing a darkened range of view 260 of a visual field 1000. The training lens 222 may have physical and functional variations pertaining to the size and/or location of the lower tinted portion or region 224 and/or the degree of transparency of the lower tinted portion or region 224. For example, the higher up the lens 222 the tinting of the lower portion or region 224 extends the greater the darkened range 260 of the visual field 1000. In addition, the darker the tinting of the lower tinted portion or region 224 is the harder it will be for a wearer of the training goggles 200 to see through the lower portion tinted portion or region 224 of the training lens 222.

Figure 4A:
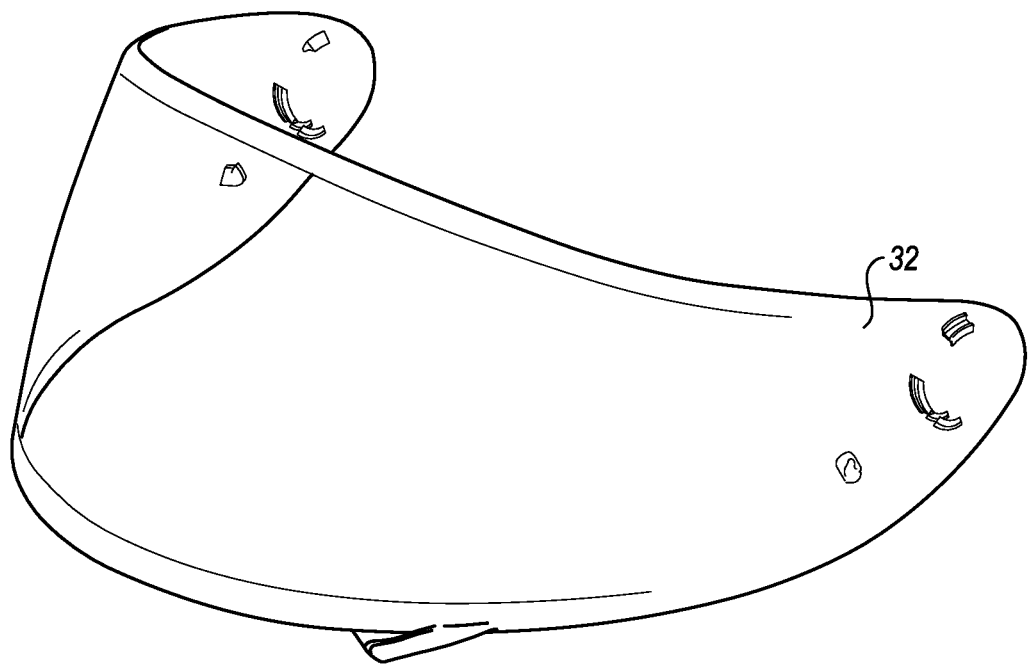
FIG. 4A illustrates a front perspective view of a common face shield lens of a sports helmet of the prior art.
Figure 4B:
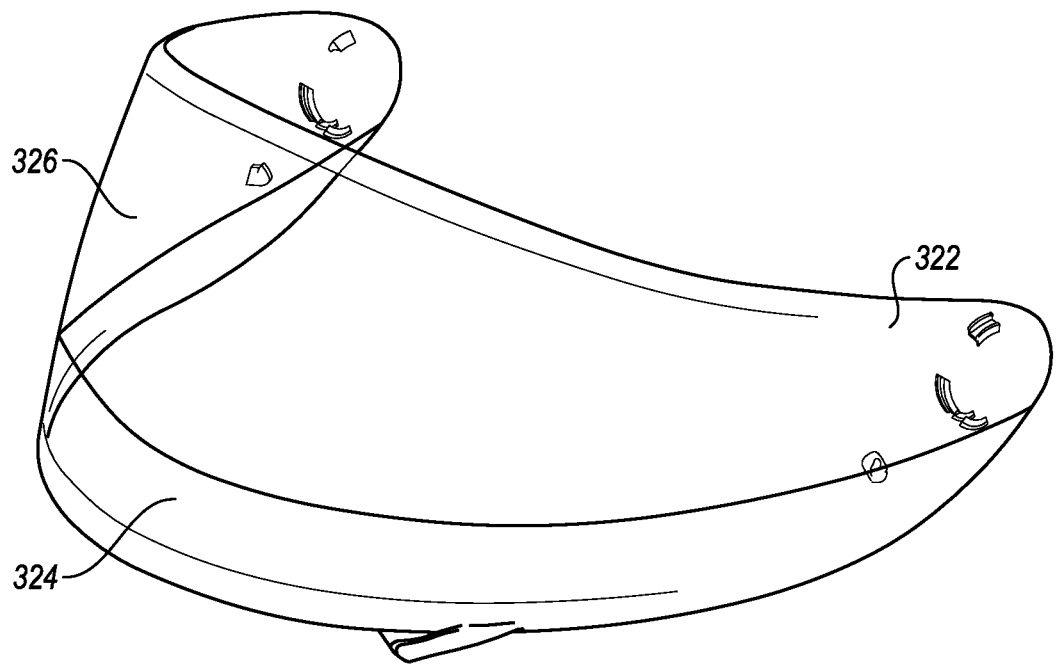
FIG. 4B illustrates a front perspective view of an embodiment of a training face shield lens configured for operation with a sports helmet.

Embodiments of a training lens may comprise other forms of eye protection (or eyewear). For instance, it is common for motorcycle helmets to include a visor or shield, such as the common face shield lens 32 of a motorcycle helmet 30 (not shown), of the prior art, that is depicted in FIG. 4A. Vastly different from the common face shield lens 32 of the prior art, a tinted training face shield lens 322, as depicted in FIG. 4B, may include a lower tinted portion 324 and an upper non-tinted (or less-tinted) portion or region 326. In a manner similar to the training lens 222 of training goggles 200, the tinted lower portion or region 324 of embodiments of training face shield lens 322 may be less transparent than the upper portion or region 326. The tinted lower portion or region 324 may comprise more than 10% and less than 70% of the total surface area of the training lens 322. Likewise, tinted lower portion or region 324 may be situated on the training shield lens 322 such that roughly 10% to 85% of the of the field of view presented through the shield lens 322 to a wearer of a helmet incorporation the training lens shield 322 is observable through the lower portion or region 324. Moreover, the degree of tinting of the tinted lower portion or region 324 on the training lens 322 may vary from light tinting (almost completely transparent) to dark tinting (affording much less transparency) and may even be completely non-transparent. The first more transparent upper portion or region 326 and second less transparent and more darkly tinted portion or region 324 have a visual light transmission value, wherein the difference between the visual light transmission of the first more transparent upper portion or region 326 and second less transparent and more darkly tinted portion or region 324 is between 20% and 80%.

Figure 5A:
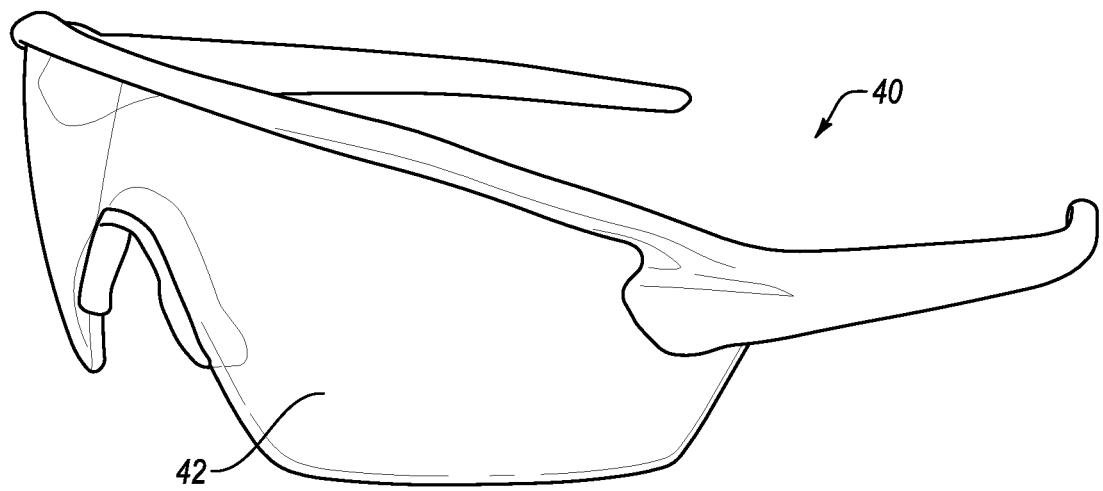
FIG. 5A illustrates a front perspective view of common glasses of the prior art.
Figure 5B:
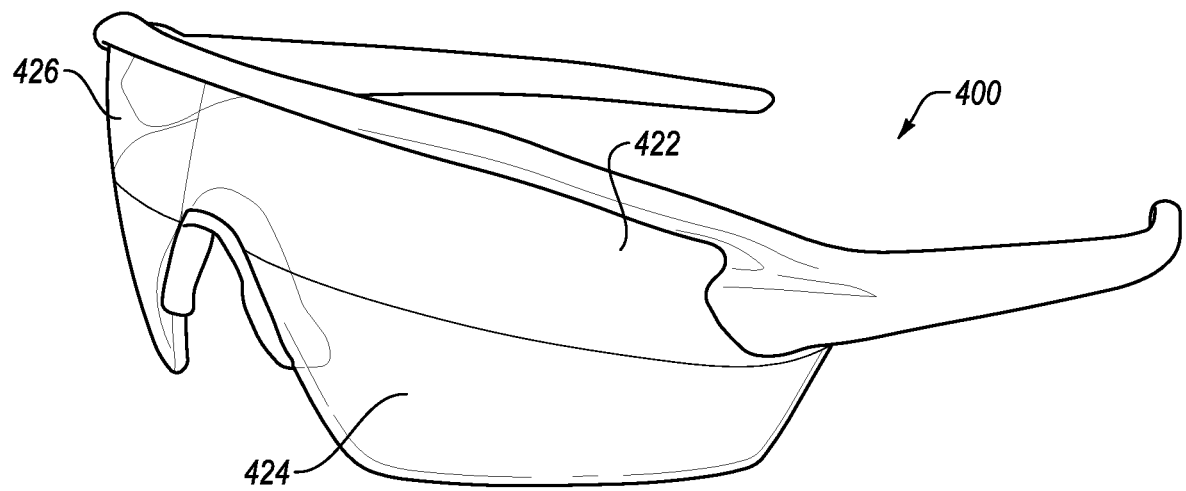
FIG. 5B illustrates a front perspective view of an embodiment of glasses including an embodiment of a training lens.
Figure 6:
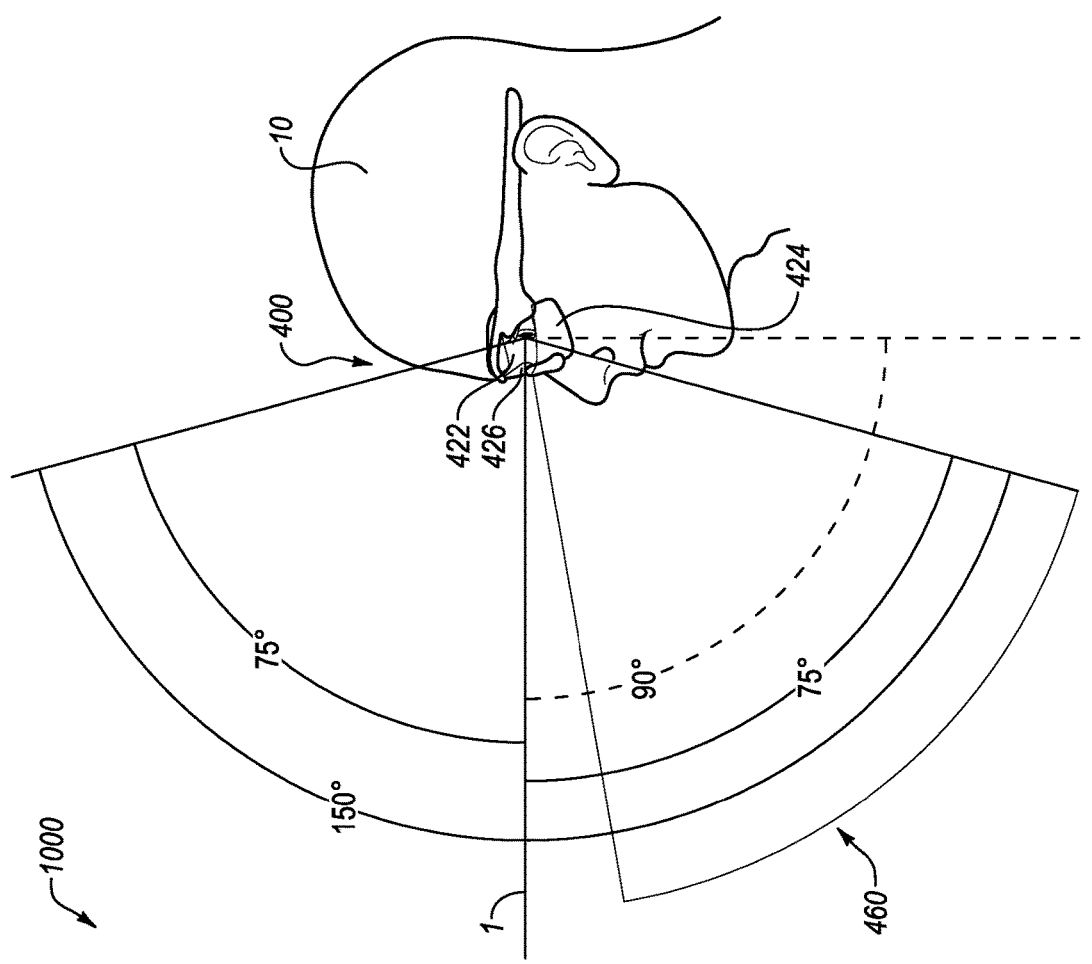
FIG. 6 illustrates a side view of a human profile wearing the embodiment of glasses of FIG. 5B having an embodiment of a training lens, and revealing a darkened range of view of a visual field.

With continued reference to the drawings, another common form of eyewear is shown in FIG. 5A, which depicts a front perspective view of common glasses 40 of the prior art. The glasses 40 may include a lens 42, through which a wearer of the glasses 40 may look to perceive a visual field. The lens 42 may be tinted, although those of ordinary skill in the art will appreciate that the tinting of the lens 42 is commonly homogeneous with a singular degree or level of transparency existent across the entire surface area of lens 42. Often the tinting is employed to help a wearer see in bright-light environments, such as out in the sun. Those of ordinary skill in the art will also recognize that other embodiments of glasses 40 may include a lens 42 having a fading gradient of tinting across the surface area of lens 42, so that one portion of the lens 42 is more transparent and the overall degree of transparency fades across the entire surface area of lens 42 terminating at a portion or region of the lens 42 that is less transparent. Such a fading gradient of tinting darkens the upper portion or region of a user's field of view. Typically the less transparent portion (or darker portion or region) of the fading gradient is existent on the upper part of the lens 42 and the more transparent portion (or lighter, clearer portion or region) is existent on the lower part of the lens 42, and in these cases the less transparent portion is for the purpose of light shading not for focus of the user. In stark contrast to typical glasses 40 having a standard lens 42 (with common tinting, if any tinting), embodiments of training glasses 400, as shown in FIG. 5B, may include a training lens 422 that includes bifurcated tinting, with an upper (non-tinted or lightly-tinted) portion or region 426 and a lower (tinted or darker tinted) portion or region 424. The tinted lower portion or region 424 may comprise 10% to 70% of the total surface area of the training lens 422. Additionally, the tinted lower portion or region may be situated on the training lens 422 such that roughly 10% to 85% of the of the field of view presented through the lens 422 to a wearer of the training glasses 400 is observable through the lower portion or region 424. If the upper portion or region 426 is tinted, the tinting is present to help a wearer primarily see clearly in brighter ambient light conditions. The bifurcated tinting configuration of the lens 422 facilitates observation training capability for users who wear the training glasses 400. Referring still further to the drawings, FIG. 6 depicts a side view of a human profile 10 wearing the embodiment of glasses 400 of FIG. 5B having an embodiment of a training lens 422, and revealing a darkened range of view 460 of a visual field 1000. The bifurcation of lens 422, particularly the delineation between the significantly tinted lower portion or region 424 and the non-tinted or lightly tinted upper portion or region 426, comprises a clear demarcation, such that there is a significantly noticeable difference in observability between the upper portion or region 426 and the lower portion or region 424. The demarcation is a substantial and significant difference of tinting and lens transparency. There may be embodiments that include a slight or small amount of fading gradient between differently tinted upper and lower portions or regions of the lens, but such fading is immediately proximate the bifurcation boundary between the upper portion or region and the lower portion or region, such that observability is starkly different through the more transparent upper portion or region of the lens and the less transparent lower portion or region of the lens. A benefit of tinted training lenses is that they encourage a user to keep a forward focus on the activity in which they are engaged. The less transparent lower portion of the lens automatically encourages the eye to look through the path of least resistance, i.e. the upper portion or region of the lens having greater transparency, thereby focusing more attention on what is ahead instead of what is immediately present.

Figure 7A:
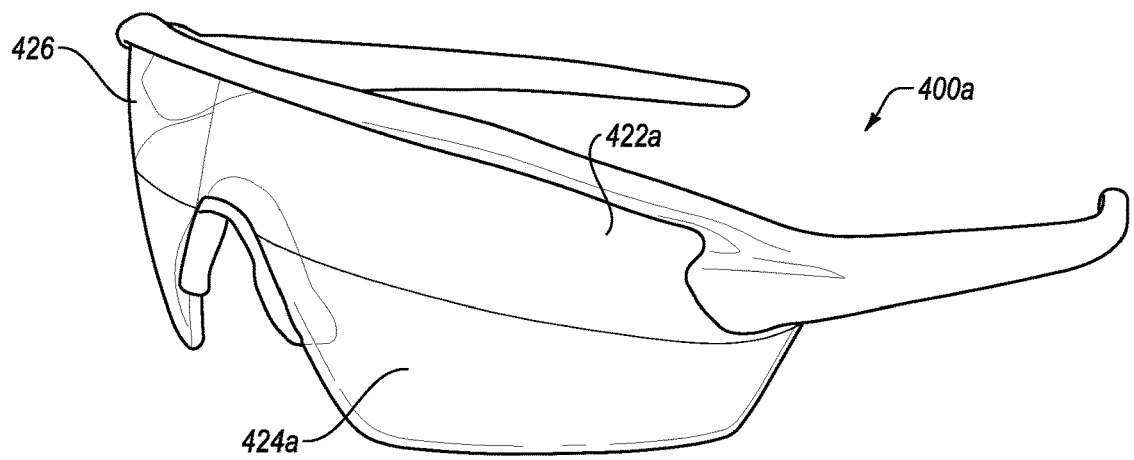
FIG. 7A illustrates a front perspective view of an embodiment of glasses including an embodiment of a training lens having "Light" or higher-transparency tinting, in the lower portion or region of the lens.
Figure 7B:
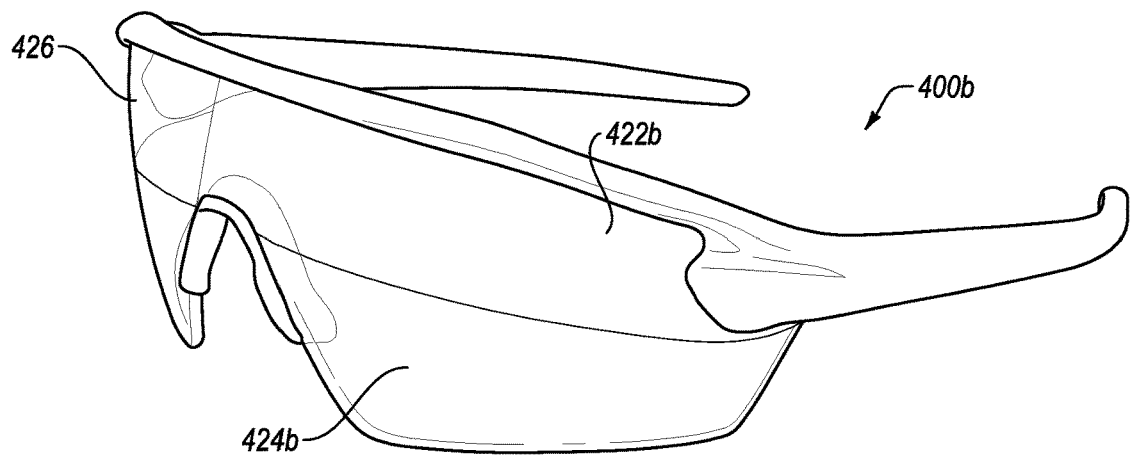
FIG. 7B illustrates a front perspective view of an embodiment of glasses including an embodiment of a training lens having "Medium" or intermediate-transparency tinting in the lower portion or region of the lens.
Figure 7C:
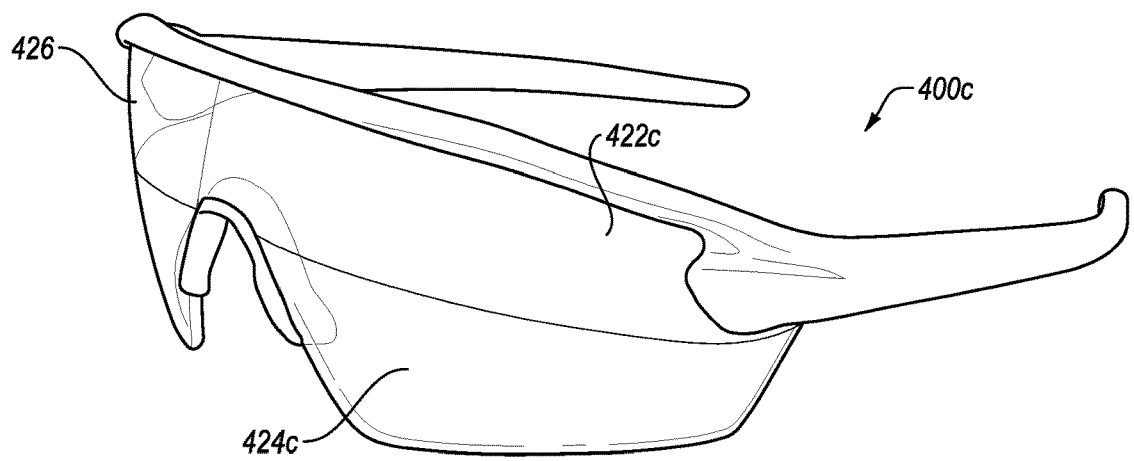
FIG. 7C illustrates a front perspective view of an embodiment of glasses including an embodiment of a training lens having "Dark" or lower-transparency tinting in the lower portion or region of the lens.
Figure 8C:
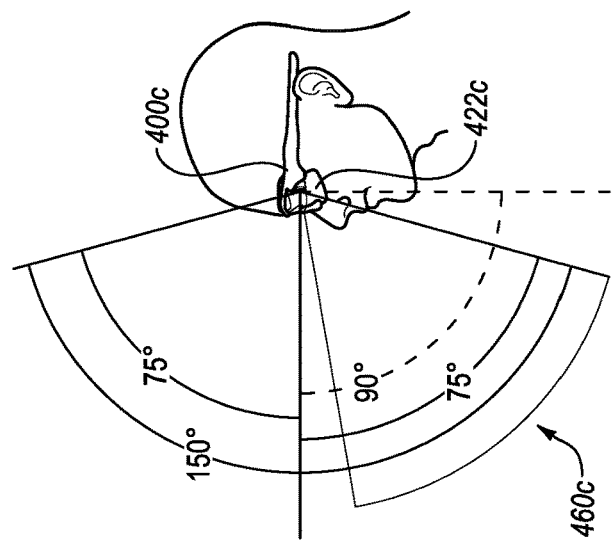
FIG. 8C illustrates a side view of a human profile wearing the embodiment of glasses of FIG. 7C having an embodiment of a Dark tinted training lens, and revealing a corresponding darkened range of view of a visual field.
Figure 8B:
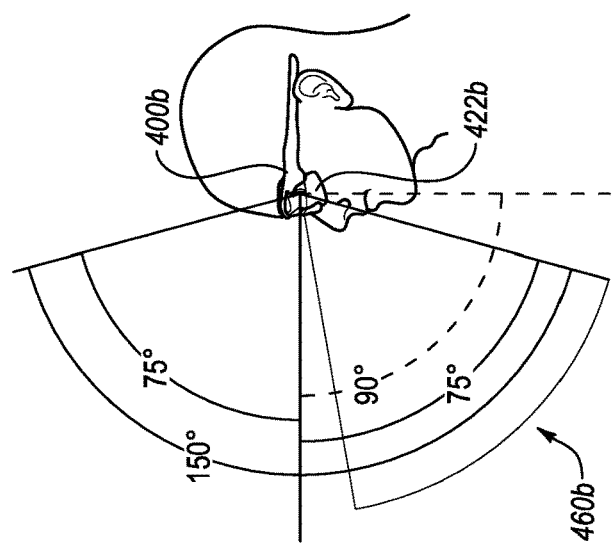
FIG. 8B illustrates a side view of a human profile wearing the embodiment of glasses of FIG. 7B having an embodiment of a Medium tinted training lens, and revealing a corresponding darkened range of view of a visual field.
Figure 8A:
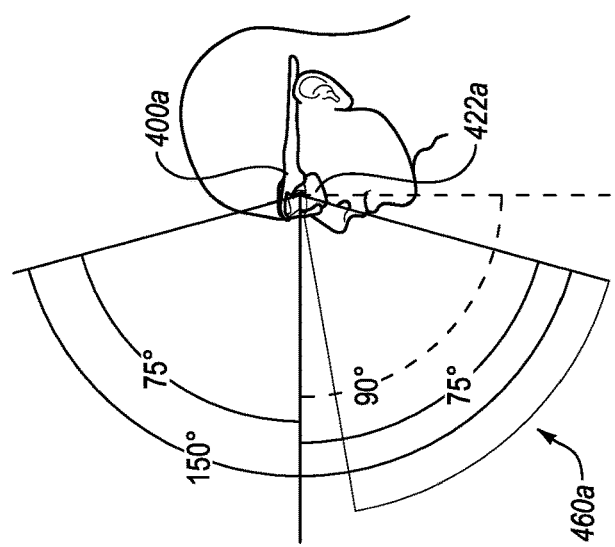
FIG. 8A illustrates a side view of a human profile wearing the embodiment of glasses of FIG. 7A having an embodiment of a Light tinted training lens, and revealing a corresponding darkened range of view of a visual field.

Embodiments of a training lens 422 may have physical and functional variations pertaining to the degree of transparency of the lower tinted portion or region 424, i.e. how dark the lower portion or region 424 is tinted. Such tinting variation is depicted in FIGS. 7A-7C, which respectively illustrate front perspective views of embodiments of glasses 400a-c respectively including embodiments of training lenses 422a-c having "Light" or higher-transparency tinting, in the lower lens portion or region 424a (FIG. 7A), having "Medium" or intermediate-transparency tinting in the lower lens portion or region 424b (FIG. 7B), and having "Dark" or lower-transparency tinting in the lower lens portion or region 424c (FIG. 7C). The first more transparent upper portion or region 426 and second less transparent and more darkly tinted portion or region 424 have a visual light transmission value, wherein the difference between the visual light transmission of the first more transparent upper portion or region 426 and second less transparent and more darkly tinted portion or region 424 is between 20% and 80%. The different tinting variations of the embodied lower portions or regions (424a-c) of the lenses (422a-c) may facilitate different observability of a visual field 1000, when worn by a user. For instance, FIG. 8A illustrates a side view of a human profile wearing the embodiment of glasses 400a of FIG. 7A having an embodiment of a Light tinted training lens 422a, and revealing a corresponding darkened range of view 460a of a visual field. Moreover, FIG. 8B illustrates a side view of a human profile wearing the embodiment of glasses 400b of FIG. 7B having an embodiment of a Medium tinted training lens 422b, and revealing a corresponding darkened range of view 460b of a visual field. In addition, FIG. 8C illustrates a side view of a human profile wearing the embodiment of glasses 400c of FIG. 7C having an embodiment of a Dark tinted training lens 422c, and revealing a corresponding darkened range of view 460c of a visual field. The darker the tinting of the lower tinted portion 424 is the harder it may be for a wearer of the glasses 400 to see through the lower portion tinted portion or region 424 of the training lens 422.

The amount of transparency in the lens, such as lens 222 and lens 422 (of both the lower portion 224, 424 and the upper portion 226, 426 can be adjusted to the specific use for which it is intended and it can also be adjusted to the needs of the specific end user. One example of a specific use comprises the utilization of the training lenses, such as lenses 222, 422, in outdoor sports. In such a situation, a darker or less transparent lower lens portion or region (424c, 224c) may be more effective in high light situations, and a lighter or more transparent lower lens portion or region (224a, 424a) may be more effective in darker lighting situations such as cloudy days, early mornings or late evenings. Embodiments of a training lens, such as lenses 222 and 422, may also be provided according to user preference. For example, in Mountain Biking or Dirt Biking a specific user may want a more or less transparent lower lens portion or region (224 and 424) depending on their skill level. A more experienced rider might be better trained at keeping their eyes up and focus forward; in this situation there would be less need for the increased training lens help through less transparency, hence a more transparent lower lens portion, such as lower lens portions or regions 224a and 424a may be effective. A less experienced rider who is not experienced in where to focus while riding might start out with a less transparent lower lens portion, such as lower lens portions or regions 224c and 424c, thereby helping force the user's eyes to focus forward more. As the lens users' skills grow and they become more accustomed to keeping their focus forward they could move to more transparency, such as lower lens portions or regions 224a-b and 424a-b. These same principles may apply to almost all activities where training lenses may be used. For instance, as training lens users seek help in learning to look ahead or keep their eyes up the users can utilize less transparent lenses. For more advanced users, who may be better at keeping proper sight lines and forward focus, more transparent lenses may serve as adequate natural reminders and aid users in looking up and/or ahead. In light of user preference, no matter what the skill level for an intended activity the responsiveness and observability of some people to different levels of transparency may be more effective than others, and thus the amount of transparency of a training lens may be customized on an individual basis.

Figure 9A:
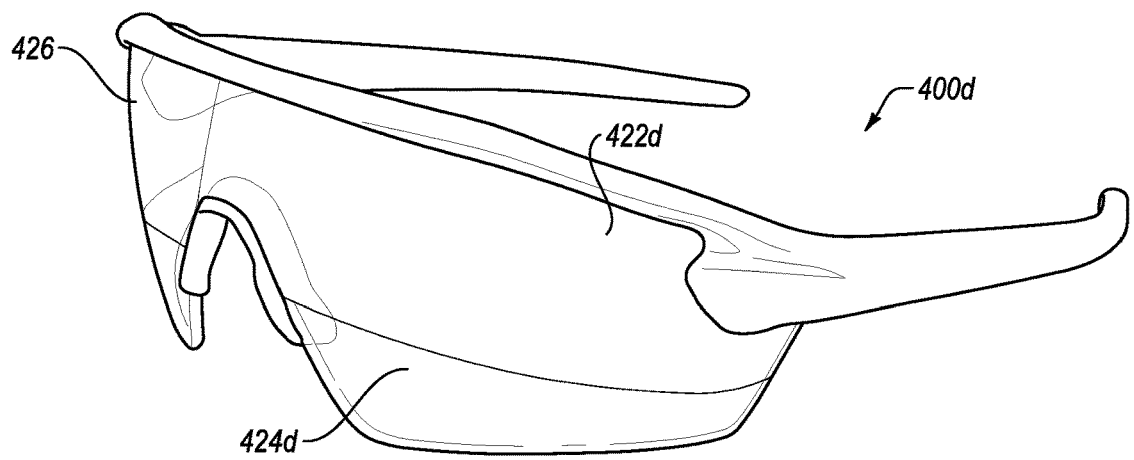
FIG. 9A illustrates a front perspective view of an embodiment of glasses including an embodiment of a training lens having a darkened or tinted portion comprising a "Short" low portion or region of the lens.
Figure 9B:
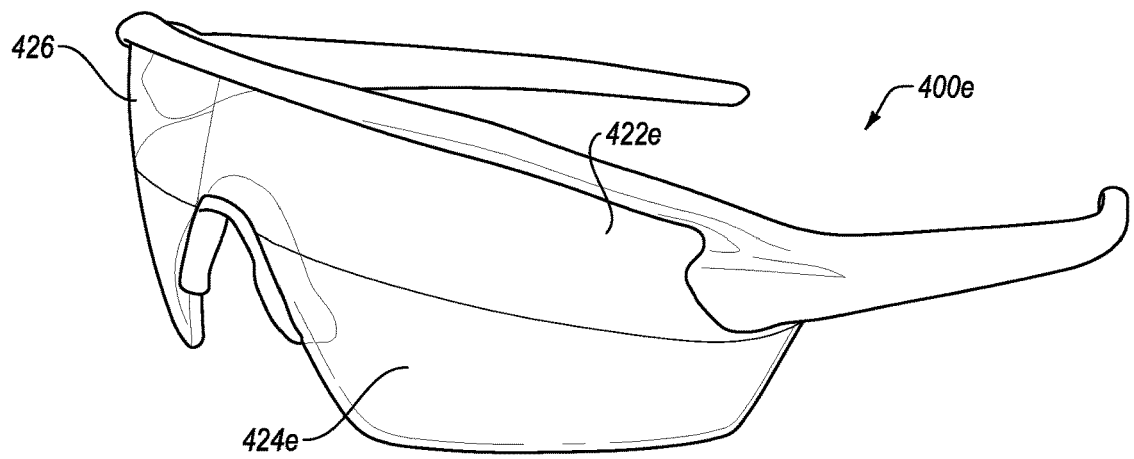
FIG. 9B illustrates a front perspective view of an embodiment of glasses including an embodiment of a training lens having a darkened or tinted portion comprising a "Medium" low portion or region of the lens.
Figure 9C:
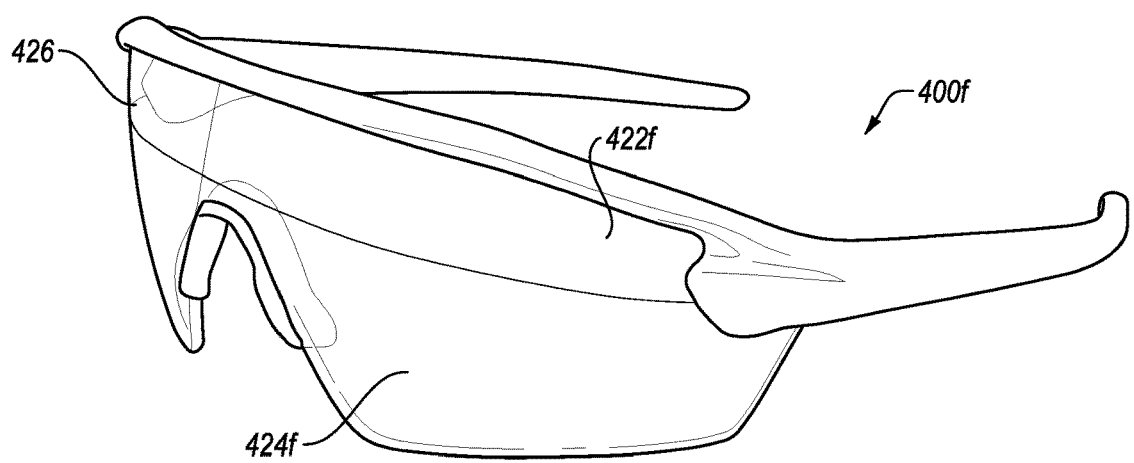
FIG. 9C illustrates a front perspective view of an embodiment of glasses including an embodiment of a training lens having a darkened or tinted portion comprising a "Tall" low portion or region of the lens.
Figure 10A:
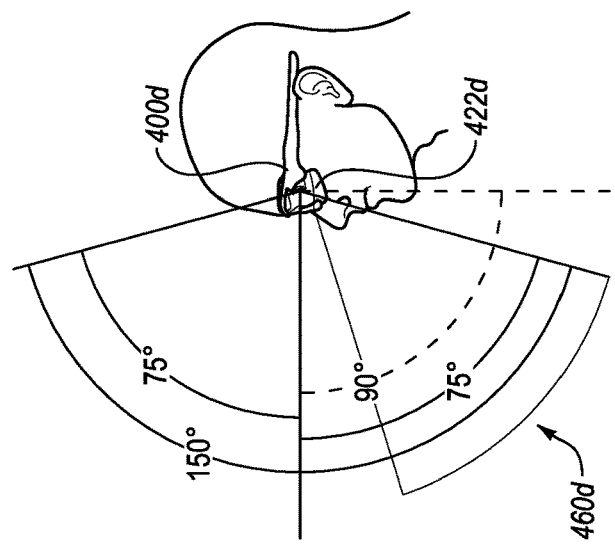
FIG. 10A illustrates a side view of a human profile wearing the embodiment of glasses of FIG. 9A having an embodiment of a Short low tinted region training lens, and revealing a corresponding darkened range of view of a visual field.
Figure 10B:
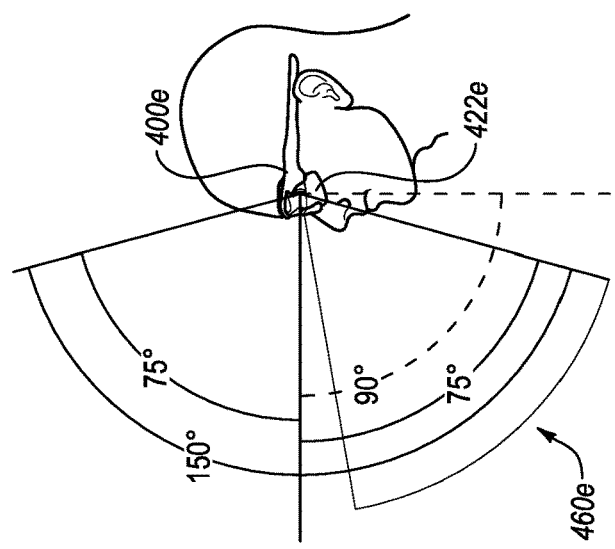
FIG. 10B illustrates a side view of a human profile wearing the embodiment of glasses of FIG. 9B having an embodiment of a Medium low tinted region training lens, and revealing a corresponding darkened range of view of a visual field.
Figure 10C:
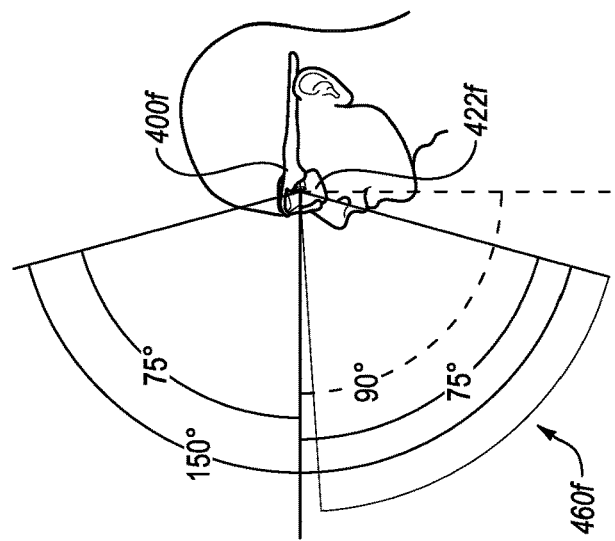
FIG. 10C illustrates a side view of a human profile wearing the embodiment of glasses of FIG. 9C having an embodiment of a Tall low tinted region training lens, and revealing a corresponding darkened range of view of a visual field.

Other physical variations of embodiments of training lenses can help facilitate further modifications to observability of a wearer, and thereby help train user observation tendencies. For example, the higher up the lens 422 the tinting of the lower portion 424 extends the greater the darkened range 460 of the visual field 1000. Such tinting height variation is depicted in FIGS. 9A-9C, which respectively illustrate front perspective views of embodiments of glasses 400d-f respectively including embodiments of training lenses 422d-f having a darkened or tinted portion comprising a "Short" low portion or region of the lens 424d (FIG. 9A), having a darkened or tinted portion comprising a "Medium" low portion or region of the lens 424e (FIG. 9B), and having a darkened or tinted portion comprising a "Tall" low portion or region of the lens 424f (FIG. 9C). In the lens 422f, the Tall low portions or regions 424f of the lens may align with the top of the nose cutout of the lens 422f. The height that the tinted lower portion or region 424 extends up the lens 422 affects observability of a wearer. For instance, FIG. 10A illustrates a side view of a human profile wearing the embodiment of glasses 400d of FIG. 9A having an embodiment of a Short low tinted portion training lens 422d, and revealing a corresponding darkened range of view 460d of a visual field. Additionally, FIG. 10B illustrates a side view of a human profile wearing the embodiment of glasses 400e of FIG. 9B having an embodiment of a Medium low tinted portion training lens 422e, and revealing a corresponding darkened range of view 460e of a visual field. Furthermore, FIG. 10C illustrates a side view of a human profile wearing the embodiment of glasses 400f of FIG. 9C having an embodiment of a Tall low tinted portion training lens 422f, and revealing a corresponding darkened range of view 460f of a visual field. The height of the lower tinted portion or region of the lens 422 may extend from roughly 10% to 85% of the lower range of a user's field of view.

Figure 11:
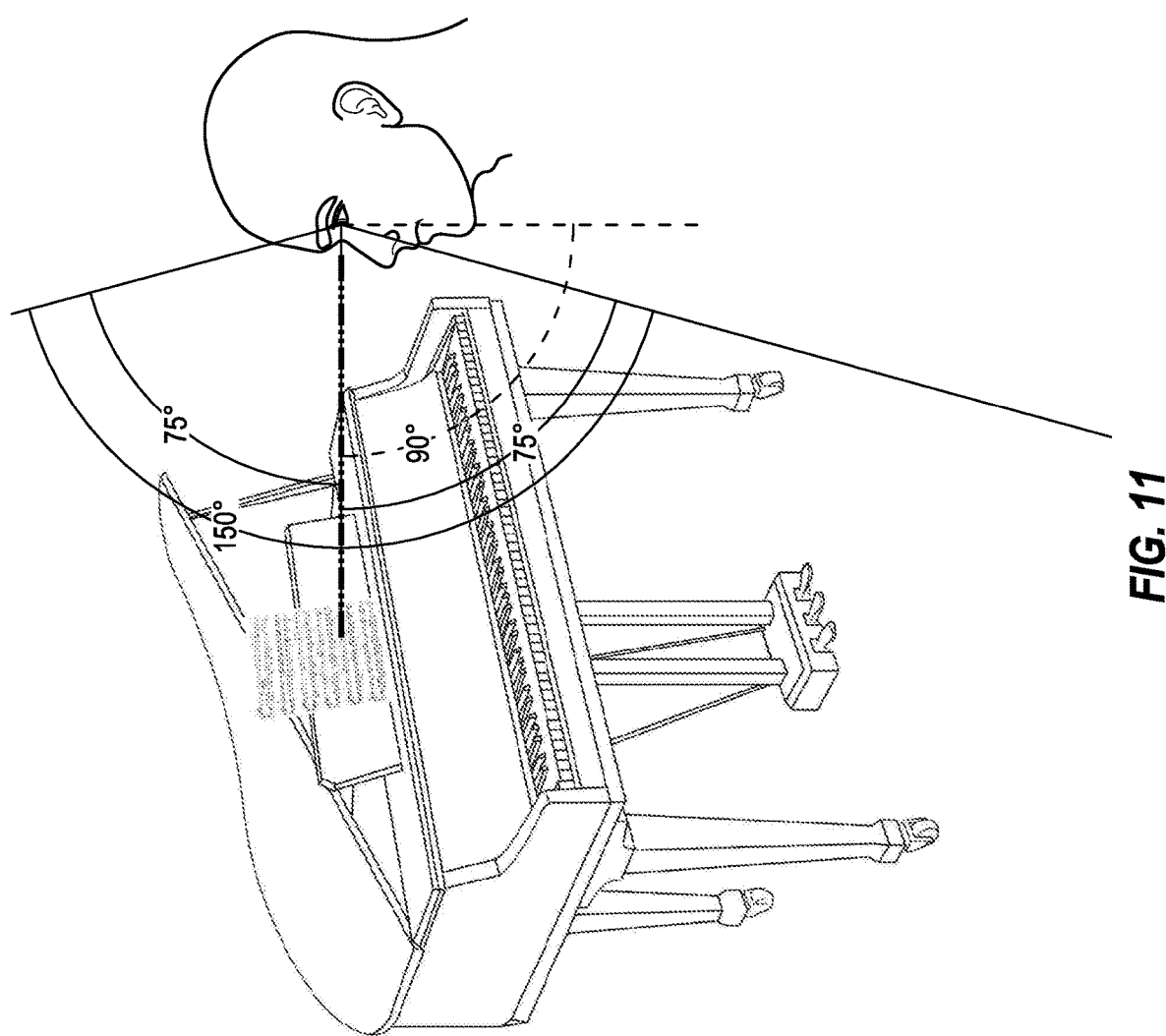
FIG. 11 illustrates a side view of a human profile revealing common range of view of a visual field, wherein the visual field includes a piano that the human intends to play.
Figure 12:
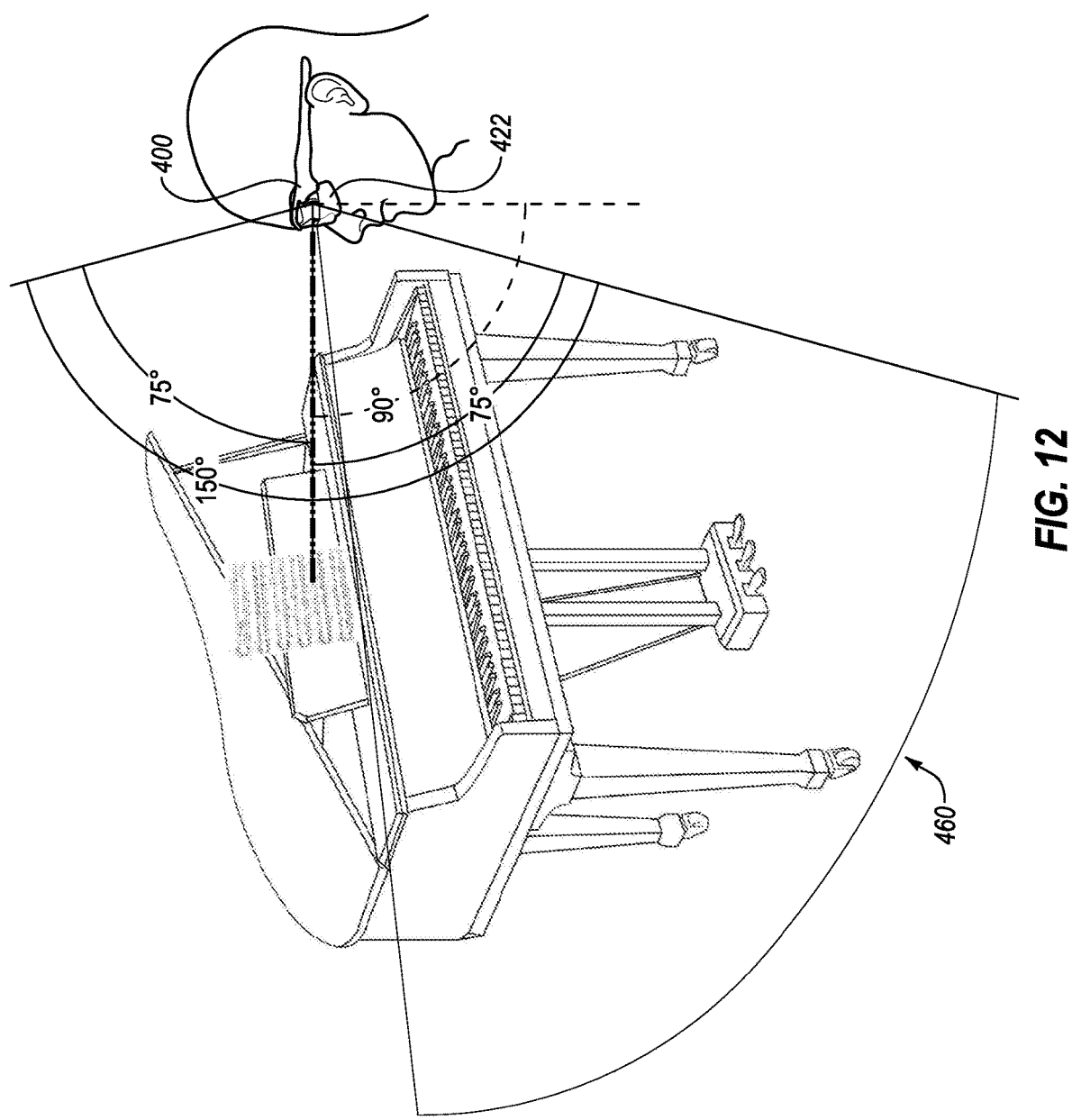
FIG. 12 illustrates a side view of a human profile wearing the embodiment of glasses having an embodiment of a training lens, and revealing a darkened range of view of the visual field of FIG. 11 including a darkened keyboard portion of the piano that the human intends to play.

As with the level of transparency of training lenses discussed above, individual users may have a personal preference as to how much of the lens being shaded (i.e. the height and surface are of the lower tinted portion, such as lower portions or regions 224 and 424) is best and most beneficial to them. However there are also times when specific activities may warrant more or less of the surface area of the lower portion of the lens to be adjusted to different levels of transparency. For example, a dirt bike rider is typically moving at higher speeds than a hiker. Therefore keeping a greater degree of focus forward may be more important for the dirt bike rider so rider does not come into obstacles that the rider was not pre warned of and therefore prepared for. In this case a greater portion of the lower lens being shaded (such as lens region 424d) would force the rider's eyes further ahead and could give a greater benefit. Moreover, in another example of personalized structure and function pertinent to training lens embodiments, a rock climber may need to keep from looking down and therefore desire a higher portion of the lower lens to be shaded (such as lens region 424d), thereby aiding in keeping climber's eyes up more. In addition, because rock climbing sometimes requires looking down to find foot holds, the user may also want more transparency in the darker portion of the lens than other sports would typically desire. Hence, a lens combining the transparency of lens 422a with the surface area of tinting of lens 422d may effectively aid in keeping the climber's eyes and focus up more naturally, but also allows the climber to more easily sight footholds when needing to look down. With continued reference to the drawings, FIG. 11 illustrates a side view of a human profile 10 revealing common range of view of a visual field, wherein the visual field includes a piano that the human intends to play. Training lenses may be utilized to help train the piano player to focus on an effective portion of the visual field. In this instance, it is beneficial for the piano player to focus on the sheet music located on the stand of the piano, rather than look down at their fingers and the piano keyboard. Hence, to help train a piano player to look up at the sheet music, an embodiment of a training lens may be utilized. Such an embodiment is shown in FIG. 12, which illustrates a side view of a human profile wearing the embodiment of glasses 400 having an embodiment of a training lens 422, and revealing a corresponding darkened range of view 460 of the visual field of FIG. 11 including a darkened keyboard portion of the piano that the piano player intends to play. When the keyboard is darkened by the tinted lower portion or region 424 of the training lens 422 of the glasses 400 worn by the piano player, the piano player more naturally tends to focus on the sheet music that is not darkened, because the field of view is perceived through the upper non-tinted portion or region 426 of the training lens 422 of the glasses 400. Repetitive use of the training glasses 400 when practicing the piano will more effectively train the piano player to keep their focus on the sheet music, rather than down on their fingers and the keyboard. Tinted training eyewear, such as glasses 400, help take the focus off of the arms, legs, hands and feet when engaged in learning activities that involve the use of limb and appendage muscle memory. When playing the piano or organ, the pianist often first learns to correspond music symbols to keys on the piano, as they become familiar with the keys they often then have to learn to not look at their hands or feet and must learn muscle memory in order to keep focus on the music. The darker tinted lower portion or region 424 of the lens 422 does not eliminate the view of the hands but discourages looking down, at the same time the lighter upper portion or region 426 of the lens 422 naturally encourages the eyes to keep looking up or forward. This concept and benefit applies to learning many instruments and aiding in developing muscle memory.

Figure 13:
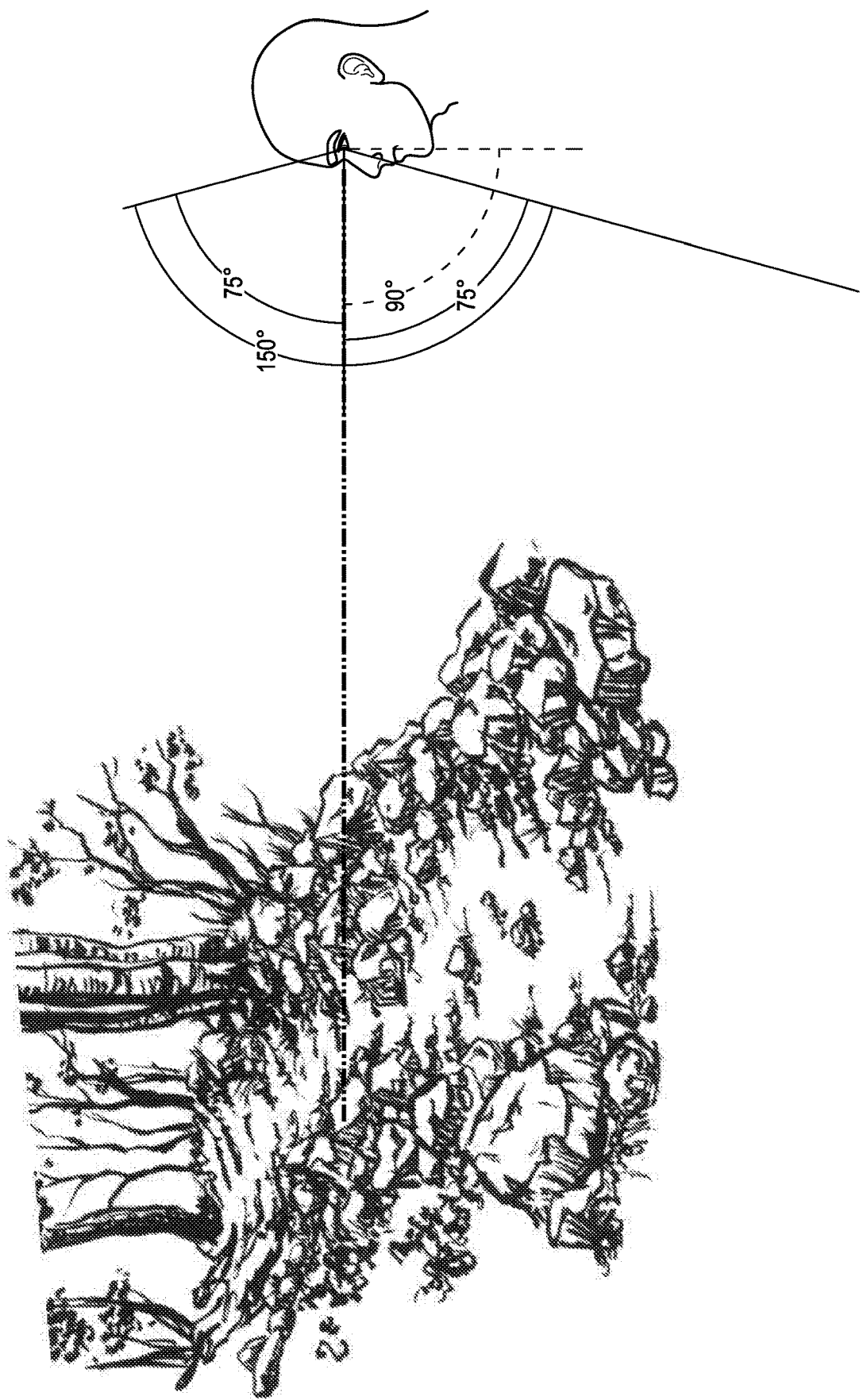
FIG. 13 illustrates a side view of a human profile revealing common range of view of a visual field, wherein the visual field includes a course or terrain that the human intends to traverse.

In a similar manner and with continued reference to the drawings, FIG. 13 illustrates a side view of a human profile revealing common range of view of a visual field, wherein the visual field includes a course or terrain that the human intends to traverse. Those of ordinary skill in the relevant are will recognize that there are several ways the terrain may be traversed, such as by hiking or running through it, mountain biking through it, riding through it in an ATV, etc. However, for exemplary purposes, it may be considered that the person intends to traverse the terrain while riding a dirt bike motorcycle. As discussed, a training lens may be employed to assist the focus of the rider, while traversing the terrain. In this regard, FIG. 14 illustrates a side view of a human profile (the motorcycle rider in this instance) wearing the embodiment of goggles 200 having an embodiment of a training lens 222, and revealing a darkened range of view 260 of the visual field of FIG. 13 including a darkened portion of the course or terrain that the dirt bike rider intends to traverse. When the nearby portion of the terrain is darkened by the tinted lower portion or region 224 of the training lens 222 of the goggles 200 worn by the rider, the rider more naturally tends to focus on the terrain that is farther ahead and not darkened, because the rider's field of view is more naturally perceived through the upper non-tinted portion or region 226 of the training lens 222 of the goggles 200. Repetitive use of the training goggles 200 when the dirt bike rider is out motorcycling over various terrain will more effectively train the rider to keep their focus on the terrain ahead, rather than looking at the nearby terrain and losing the ability to benefit from forward focus.

Tinted training lenses may help eliminate the sense of vertigo or dizziness in mountain or steep hillside activities. This can apply to hiking, biking, motor sports and other activities. For instance, when riding a mountain bike or motorcycle across a steep hillside many riders may be confronted with the sensation of dizziness or vertigo due to the fact that a steep upper hillside on one side is providing the sensation of movement while on the other side the riders may see sky, and sometimes with clouds, birds or other objects having movement in the opposite direction to the hillside. Variations of these situations often cause several negative side effects including dizziness and vertigo. Another challenge aside from these sensations is due to fear the individual may lean toward the hillside which often causes them to lose balance or even hit the hill side causing an over correction or even a crash. Often times hikers under the same steep hillside circumstances experience similar sensations as bikers, such as described above, and this is especially true for both activities (hiking and biking) when narrow trails are being traversed. A significant benefit of tinted training eyewear, such as goggles 200 having training lens 222 or glasses 400 having training lens 422, in these hillside circumstances, is that the training lenses help the individuals keep a forward focus instead of focusing on the immediate imbalanced surrounds. Dizziness may be dispelled and the sense of flying may be eliminated, while focus is kept forward and balance is maintained. With the lenses in use by wearers, vision of immediate surrounds is not eliminated but, instead, the training lenses naturally encourage the wearer's eyes to give more focus on what will not distract or cause unwanted sensations. The training lenses also help give the wearers a greater sense of confidence and security, because, by looking forward, the wearers observe the trail ahead and overcome the fear that would normally encourage them to hold tight to the hillside and cause over correction or running into hillside obstacles; thereby helping to eliminate stumbling or crashes.

In addition, tinted training lenses may help individuals keep their "head in the game", so to speak, by helping to eliminate over-stimulus and other distractions that lead to fear and loss of a general feeling of confidence and well-being. This can be especially important in dangerous activities where loss of focus or confidence could mean injury. For example, in addition to the activities described above, climbing activities and slack lining or tight roping can also cause extreme visual over-stimulation due to what is below rather than what is above or ahead, essentially the visual stimuli from below distracts from the real goal. Tinted training lenses naturally aid the individual to keep an up or forward focus without eliminating the view of the rest of the environment. This narrowing of the range of view also aids in keeping the individual from endangerment through loss of focus or fear.

While this disclosure has been described in conjunction with the specific embodiments outlined above, it is evident that many alternatives, modifications and variations will be apparent to those skilled in the art. For example, tinted training lenses may be utilized to assist those recovering from strokes or other muscular control loss to focus more intently on features that will more effective assist their recovery. Moreover, tinted training lenses may be worn by those with autism, to decrease visual stimulus, by darkening portions of a range of view through employment of tinted regions of the visual observation training lenses. Accordingly, the preferred embodiments of the present disclosure as set forth above are intended to be illustrative, not limiting. Various changes may be made without departing from the spirit and scope of the present disclosure, as required by the following claims. The claims provide the scope of the coverage of the present disclosure and should not be limited to the specific examples provided herein.

What is claimed is:

1. A visual field observation training lens comprising:
   a total surface area;
   a first transparency region that is disposed at an upper portion of the visual field observation training lens; and a second transparency region that is disposed at a lower portion of the visual field observation training lens;

wherein the second transparency region is less transparent than the first transparency region, wherein the visual field observation training lens comprises a top edge portion, a bottom edge portion that is disposed substantially opposite to the top edge portion, a first lateral edge portion, and a second lateral edge portion that is disposed substantially opposite to the first lateral edge portion, wherein an upper edge of the second transparency region comprises a delineation line at an interface between the second transparency region and the first transparency region, and wherein the delineation line of the second transparency region that is disposed at the lower portion of the visual field observation training lens extends horizontally across the visual field observation training lens from the first lateral edge portion to the second lateral edge portion.

2. The training lens of claim 1, wherein the first lateral edge portion of the visual field observation training lens is configured to be disposed near a right side of a user's face during use, and wherein the second lateral edge portion of the visual field observation training lens is configured to be disposed near a left side of the user's face during use.

3. The training lens of claim 1, wherein the first lateral edge portion of the visual field observation training lens is configured to be disposed near a nose bridge of a user during use, and wherein the second lateral edge portion of the visual field observation training lens is configured to be disposed near at least one of (i) a right side and (ii) and left side of a face of the user during use.

4. The training lens of claim 1, wherein the delineation line comprises a contiguous line that extends across the visual field observation training lens above a nose cutout that is defined in the visual field observation training lens.

5. The training lens of claim 1, wherein the first transparency region and the second transparency region each have a visual light transmission value, and wherein a difference between the visual light transmission of the first transparency region and the second transparency region is between 31% and 80%.

6. The training lens of claim 1, wherein the delineation line comprises an unbroken line that extends from the first lateral edge portion to the second lateral edge portion of the visual field observation training lens, and wherein the visual field observation training lens comprises a face shield.

7. The training lens of claim 1, wherein the delineation line is broken by a nose cutout of the visual field observation training lens.

8. A visual field observation training lens comprising: bifurcated tinting, wherein a lower portion of the visual field observation training lens is more tinted than is an upper portion of the visual field observation training lens, wherein the bifurcated tinting of the visual field observation training lens comprises a demarcation boundary line at an upper edge of the lower portion that is more tinted, such that there is a significantly noticeable difference in observability between the lower portion that is more tinted and the upper portion, wherein the visual field observation training lens comprises a top edge portion, a bottom edge portion that is disposed substantially opposite to the top edge portion, a first lateral edge portion, and a second lateral edge portion that is disposed substantially opposite to the first lateral edge portion, wherein the demarcation boundary line at the upper edge of the lower portion that is more tinted extends horizontally across the visual field observation training lens from the first lateral edge portion to the second lateral edge portion, wherein the visual field observation training lens defines a nose cutout, and wherein the demarcation boundary line at the upper edge of the lower portion that is more tinted runs adjacent to an apex of the nose cutout.

9. The training lens of claim 8, wherein the nose cutout bisects the demarcation boundary line.

10. The training lens of claim 8, wherein the lower portion that is more tinted comprises less than 25% of a total surface area of the visual field observation training lens.

11. The training lens of claim 8, wherein the lower portion that is more tinted and the upper portion are on separate lens layers that are placed together to form a composite lens.

12. The training lens of claim 8, wherein the demarcation boundary line at the upper edge of the lower portion that is more tinted comprises a continuous line that extends above the nose cutout.

13. The training lens of claim 8, wherein the lower portion that is more tinted is situated on the visual field observation training lens such that between 50% and 85% of an observable field of view is tinted and presented through the lower portion of the field observation training lens to a wearer of the field observation training lens.

14. The training lens of claim 8, wherein the lower portion that is more tinted is coupled to eyewear, and wherein the lower portion that is more tinted is removable from the eyewear.

15. The training lens of claim 8, wherein the lower portion that is more tinted is configured to rotate with respect to a mounting portion that is configured to couple the visual field observation training lens to a head of a user.

16. A visual field observation training lens comprising:
a total surface area;
a first transparency region that is disposed at an upper portion of the visual field observation training lens; and
a second transparency region that is disposed at a lower portion of the visual field observation training lens;

wherein the second transparency region is less transparent than the first transparency region, wherein the second transparency region comprises 10% to 70% of the total surface area of the visual field observation training lens, wherein the visual field observation training lens comprises a top edge portion, a bottom edge portion that is disposed substantially opposite to the top edge portion, a first lateral edge portion, and a second lateral edge portion that is disposed substantially opposite to the first lateral edge portion, wherein an upper edge of the second transparency region comprises a delineation line at an interface between the second transparency region and the first transparency region, wherein the delineation line of the second transparency region that is disposed at the lower portion of the visual field observation training lens extends horizontally across the visual field observation training lens from the first lateral edge portion to the second lateral edge portion, and wherein the delineation line comprises at least one of (i) a straight line and (ii) an arched line.

17. The training lens of claim 16, wherein the second transparency region at the lower portion comprises less than 25% of the total surface area.

18. The training lens of claim 16, wherein the second transparency region at the lower portion comprises between 50% and 70% of the total surface area.

19. The training lens of claim 16, wherein the visual field observation training lens defines a nose cutout, and wherein the delineation line at the upper edge of the second transparency region that is disposed at the lower portion runs adjacent to an apex of the nose cutout.

20. The training lens of claim 16, wherein a difference between visual light transmission of the first transparency region and the second transparency region is between 31% and 80%.

* * * * *